(12) United States Patent
Lorant

(10) Patent No.: US 6,620,855 B2
(45) Date of Patent: *Sep. 16, 2003

(54) PRESSURIZED DEVICE COMPRISING AN ULTRAFINE FOAMING OIL-IN-WATER EMULSION AND USE OF THIS EMULSION IN CLEANSING AND CARE OF SKIN

(75) Inventor: Raluca Lorant, Thiais (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/981,761

(22) Filed: Oct. 19, 2001

(65) Prior Publication Data

US 2002/0045670 A1 Apr. 18, 2002

Related U.S. Application Data

(63) Continuation of application No. 08/813,036, filed on Mar. 6, 1997, now Pat. No. 6,333,362.

(30) Foreign Application Priority Data

Mar. 7, 1996 (FR) ............................................. 96 02898

(51) Int. Cl.$^7$ ............................. C09K 3/30; A61K 7/00; A61K 9/12
(52) U.S. Cl. ............................ 516/8.1; 424/45; 424/47; 510/130; 510/135; 510/140
(58) Field of Search ............................. 516/8.1, 14, 58, 516/74; 424/45, 47; 510/130, 135, 140

(56) References Cited

U.S. PATENT DOCUMENTS

| | | | |
|---|---|---|---|
| 3,840,465 A | 10/1974 | Knowles et al. ............... | 424/47 |
| 3,959,160 A | 5/1976 | Horsler et al. ............... | 510/140 |
| 3,970,584 A | 7/1976 | Hart et al. ................... | 252/305 |
| 4,536,323 A | 8/1985 | Stopper ....................... | 252/305 |
| 4,808,388 A | 2/1989 | Beutler et al. ................. | 424/47 |
| 5,106,624 A | 4/1992 | Bertini ......................... | 424/401 |
| 5,160,665 A | 11/1992 | Owada et al. ............... | 252/307 |
| 5,279,819 A | 1/1994 | Hayes ......................... | 424/45 |
| 5,352,437 A | 10/1994 | Nakagawa et al. .......... | 424/401 |
| 5,484,597 A | 1/1996 | Slavtcheff et al. ........... | 424/401 |
| 5,496,538 A | 3/1996 | Zimmerman et al. ......... | 424/45 |
| 5,656,200 A | * 8/1997 | Boettcher et al. ............. | 516/14 |
| 5,690,946 A | 11/1997 | Koulbanis et al. .......... | 424/401 |
| 6,045,779 A | 4/2000 | Mueller et al. ............... | 424/47 |
| 6,126,920 A | 10/2000 | Jones et al. .................... | 424/45 |
| 6,333,362 B1 | * 12/2001 | Lorant ......................... | 516/8.1 |

FOREIGN PATENT DOCUMENTS

| | | |
|---|---|---|
| CA | 1334458 | 2/1995 |
| DE | A 4243272 | 6/1994 |
| DE | A 4318171 | 12/1994 |
| EP | A 0345586 | 12/1989 |
| EP | A 0612514 | 8/1994 |
| EP | A 0641557 | 3/1995 |
| WO | WO A 9216188 | 10/1992 |
| WO | WO 94/16668 | * 8/1994 |
| WO | WO A 9505796 | 3/1995 |
| WO | WO A 6517163 | 6/1995 |
| WO | WO A 9602225 | 2/1996 |
| WO | WO 96/11162 | 4/1996 |
| WO | WO 96/27376 | 9/1996 |

OTHER PUBLICATIONS

McCutcheon's vol. 1: Emulsifiers & Detergents North American Edition 1993 ( McCutcheon Division, MC Publishing Co., Glen Rock NJ, USA, copyright 1993) p. 63, Jan. 1994.*

English language Derwent Abstract No. 91–270690 of JP 3178331, Week 9137.

English language Derwent Abstract of DE–A–4243272, AN 94–209627/26, Week 9426.

English language Derwent Abstract of DE–A–4318171, AN–95–014884/03, Week 9503.

English language Derwent Abstract of EP–A–0641557, AN–95–099980/14, Week 9514.

PTO 98–1147 translation of De 43 18 171, 1/98.

Myers, "Surfactant Science and Technology," $2^{nd}$ ed. (VCH Publishers, Inc., NY, NY copyright 1992) Month unknown. pp. 148–155 and 240–241.

McCutcheon's vol. 1: Emulsifiers & Detergents 1993 North American Edition (McCutcheon Division, MC Publishing Co., Glen Rock, NJ Copyright 1993) Month unknown. pp. 86 and 108.

M. Rosen, "Surfactants and Interfacial Phenomena" (John Wiley & Sons, NY, NY, Copyright 1978) Month unknown. p. 224.

Myers, "Surfactant Science and Technology," (VCH Publishing, NY, NY, copyright 1992) Month unknown. p. 151.

Shinoda et al., "Emulsions and Solubilization," (John Wiley & Sons, NY, NY, copyright 1986) Month unknown. p. 5.

WPIDS on STN, Week 9514, London: Derwent Publications Ltd., AN—95 106622, WO 9505769 A1 (Sixtensson) abstract.

WPIDS on West, week 8950, London: Derwent Publications LTD., AN—89 364978, CA 1,334,458 C or DE 38 191 93 A (Henkel) abstract.

* cited by examiner

Primary Examiner—Daniel S. Metzmaier
(74) Attorney, Agent, or Firm—Finnegan Henderson Farabow Garrett & Dunner LLP

(57) ABSTRACT

A pressurized device comprising an "ultrafine" foaming oil-in-water emulsion wherein the particle size of the oil particles constituting the oil phase ranges from 50 to 1000 nm, the ultrafine emulsion being preferably obtained according to the so-called "phase inversion" technique. These ultrafine oil-in-water emulsions can be employed in particular for cleansing and care of the skin and they are rich in oils, fluid, pressurizable, foaming and translucent.

21 Claims, No Drawings

PRESSURIZED DEVICE COMPRISING AN ULTRAFINE FOAMING OIL-IN-WATER EMULSION AND USE OF THIS EMULSION IN CLEANSING AND CARE OF SKIN

This application is a continuation of application Ser. No. 08/813,036, filed on Mar. 6, 1997, now U.S. Pat. No. 6,333,362 B1.

The invention relates to new pressurized devices containing oil-in-water emulsions that have a good ability to foam, and the use of such an emulsion for topical uses, in particular, for cleansing and care of the skin.

Cleansing of the skin is very important for facial care. It must be as effective as possible because the fatty residues, such as the excess of sebum, the remainders of cosmetic products employed daily, and the make-up products, especially the water-resistant "waterproof" products, accumulate in skin folds and can block the pores of the skin and result in the appearance of pimples.

Two major types of skin-cleansing products are known: foaming detergent aqueous lotions and gels and rinsable cleansing anhydrous oils and gels.

Foaming detergent aqueous lotions and gels have a cleansing action by virtue of the surfactants therein which suspend the fatty residues and the pigments of the make-up products. They are effective and cosmetically pleasant because they foam and they are easily removed. Insofar as they do not contain any cosmetic oil, they have the disadvantage of drying the skin by their dilapidating action. This is the case, for example, with the products described by document WO95/05796, which teaches skin-cleansing lotions which are very fluid and pressurizable and which produce an attractive foam. These products, however, destroy the hydro-lipid film of the skin and leave the skin clean, but rough.

Rinsable anhydrous oils and gels have a cleansing action by virtue of the oils present in these formulations. These oils make it possible to solubilize the fatty residues and to disperse the make-up pigments. These products are effective and well tolerated by the skin. They have the disadvantage of being heavy, of not foaming and of not imparting a sensation of coolness when applied, and this is disadvantageous from a cosmetic viewpoint.

Attempts have been made to solve these technical problems by producing creams and milks for removing make-up, simultaneously containing oils, emulsifiers and detergent surfactants in a quantity which is sufficiently low so as not to destabilize the emulsion. Despite their good effectiveness, these products are not foaming and have an insufficient rinsability, which makes it necessary to use an additional detergent tonic lotion to complete the rinsing and the removal of the soiling. In addition to its astringent nature, the use of this second product can, in the long term, result in drying of the skin.

What is sought after are foaming detergent products which are completely water-rinsable, containing hydrophilic surfactants and oils which simultaneously make it possible to optimize the cleansing of the skin and to hydrate and to nourish the latter in order to avoid any drying-out phenomenon.

Oils cannot merely be introduced into a detergent aqueous lotion or gel in order to produce a product which cleanses the skin without drying it out. In fact, oils have a tendency to inhibit the foaming properties of these formulations; it is said that oils "kill" the foam. In addition, the oil dispersion is unstable. Foaming emulsions, for example, emulsions for removing make-up are known, for example, from document WO95/17163. A product of this type is very mild and very well tolerated by the skin, but the foamability of these emulsions is low because of the presence of oils. Moreover, these emulsions are always opaque and relatively thick, and this does not allow them to be packaged in pressurized receptacles.

In the same way, foaming surfactants cannot merely be introduced into conventional creams or milks for removing make-up, which are oil-in-water emulsions, in order to obtain good foamability. When introduced in concentrations higher than 5% by weight, these surfactants result in the breaking of these emulsions, because they disturb the interfacial film formed by the emulsifier around the oil droplets in dispersion.

In addition, attempts have been made to prepare a pressurizable product. In fact, packaging in aerosol form is particularly advantageous because it allows a controlled distribution, better conservation of the product and, in addition, they have the appearance of a plaything as seen by the user.

It is known, for example from document WO89/11907, that the phase inversion method makes it possible to prepare pressurizable, ultrafine, stable, fluid oil-in-water emulsions. These emulsions are often packaged in the form of a pressurized composition and are restored into the form of sprays, without solvent and without volatile organic compounds. However, the emulsions prepared by the phase inversion method in the prior art are nonfoaming. In fact, the surfactants employed for making emulsions capable of inverting, or PIT emulsions, are nonfoaming nonionics, essentially polyethoxylated fatty alcohols, since other surfactants do not make it possible to obtain a phase inversion. From numerous investigations, which have been carried out around this subject, it is also known that the behavior of PIT emulsions is very sensitive to the components which are incorporated therein, it being very possible for an emulsion to lose its invertible character and to become destabilized under the effect of some additives. On this subject reference may be made, for example, to the following documents: T. Mitsui et al., Bulletin of the Chemical Society of Japan, vol. 43, 3044–3048 (1970) and T. Mitsui et al., American Cosmetics and Perfumery, vol. 87, 33–36 (1972). Until these discoveries, PIT emulsions were highly valued for their fluid character which gives them a great ease of application and of spreading on the skin.

Cleansing aqueous compositions for the body and hair are also known, for example, from German document DE-A-4318171, these compositions include high proportions of ionic surfactants as well as an oil, which is introduced into the surface-active aqueous composition in the form of an ultrafine emulsion. However, this document does not mention or suggest the possibility of pressurizing such compositions.

Surprisingly and unexpectedly, the Inventor has overcome the disadvantages of the prior art by using so-called "ultrafine" specific oil-in-water emulsions (which will be denoted by O/W), wherein the size of the oil particles constituting the oil phase is within well-determined limits. The emulsions of O/W type are preferably obtained according to the so-called "phase inversion" technique, described in detail below. These ultrafine O/W emulsions can be employed in particular for the cleansing and care of the skin and are rich in oils, fluid, pressurizable, foaming, stable and translucent. They can also be pressurized and packaged in aerosol receptacles.

A subject of the present invention is thus an aerosol device comprising a pressurized receptacle provided with a means of dispensing including a valve, the receptacle containing a propellant gas and a foaming emulsion comprising:

(A) at least one cosmetic oil,
(B) at least one nonionic emulsifier having an HLB ranging from 9 to 18,
(C) at least one foaming surfactant, and
(D) water,
wherein the average size of the oil particles which constitute the oil phase of these emulsions ranges from 50 to 1000 nm.

When pressure is applied to the means of dispensing of the device according to the invention, the valve is actuated and the device restores and dispenses its contents in the form of a creamy foam. Products with such a consistency are particularly valued for the cleansing and the care of the skin or of hair.

Such a device usually contains from 0.5 to 20% of propellant gas and from 80 to 99.5% of emulsion. Any propellant gases known for such applications can be employed in the devices according to the invention. There may be mentioned, in particular, hydrocarbon gases like, for example, propane, isopropane and n-butane, isobutane and mixtures thereof; fluorine-containing gases like, for example, chlorodifluoromethane, dichlorodifluoromethane, difluoroethane, chlorodifluoroethane, dichlorotetrafluoroethane and the like, and mixtures thereof. Nitrogen and carbon dioxide and their mixtures can also be employed as propellent gases in accordance with the present invention.

The emulsions according to the invention are preferably packaged in transparent aerosol receptacles. Such receptacles are well known to a person skilled in the art and commonly employed. Reference may be made on this subject to International Patent Application No. WO95/05796, the disclosure of which is incorporated herein by reference. Such receptacles exploit the surprising nature of the invention particularly well. Through the aerosol receptacle can be seen a bluish, translucent emulsion which has a fluidity comparable with that of water, the emulsion being produced in the form of a creamy foam through the means of dispensing, and not in the form of a spray as is a priori expected.

Preferably, the Brookfield viscosity of the emulsions according to the invention is less than or equal to 20 mPa.s, and even more preferably less than or equal to 10 mPa.s.

The emulsions according to the invention preferably include:

(A) from 0.5 to 50% of at least one cosmetic oil,
(B) from 0.5 to 30% of at least one non ionic emulsifier having an HLB ranging from 9 to 18,
(C) from 1 to 40% of at least one foaming surfactant, and
(D) from 10 to 90% of water.

According to a more preferred embodiment of the invention, they include:

(A) from 10 to 30% of at least one cosmetic oil,
(B) from 2 to 10% of at least one nonionic emulsifier having an HLB ranging from 9 to 18,
(C) from 5 to 15% of at least one foaming surfactant, and
(D) from 40 to 60% of water.

Preferably, in the emulsions according to the invention, the ratio of the weight of the oil to the weight of the foaming surfactant is greater than or equal to 0.5, and more preferably greater than or equal to 1, and still more preferably greater than or equal to 2.

Another subject of the invention is new foaming, pressurizable, oil-in-water emulsions comprising:

(A) from 10 to 30% of at least one cosmetic oil,
(B) from 2 to 10% of at least one nonionic emulsifier having an HLB ranging from 9 to 18,
(C) from 5 to 15% of at least one foaming surfactant, and
(D) from 40 to 60% of water,
wherein the average size of the oil particles which constitute the oil phase of these emulsions ranges from 50 to 1000 nm.

The particle size of the oil particles of the emulsion preferably range from 70 to 350 nm and still more preferably range from 100 to 300 nm. The emulsions according to the invention are extremely stable, have a fluidity comparable with that of water and are translucent.

The emulsions according to the invention are usually characterized by the fact that their polydispersity is very low. As a general rule, approximately 90% of the oil particles of the "ultrafine" emulsions according to the invention have a size ranging from 100 nm to 300 nm. The difference in size between the largest and the smallest particles generally ranges from 20 nm to 400 nm, and preferably ranges from 30 nm to 200 nm, whereas in conventional emulsions (other than PIT emulsions or microemulsions) the difference in size between the largest and the smallest particles can reach values greater than 1000 nm.

As indicated above, the oil-in-water emulsions according to the present invention are preferably obtained according to the phase inversion technique. In its principle, this technique is well known to persons skilled in the art and is described particularly in the paper "Phase Inversion Emulsification," by Th. Förster et al., published in Cosmetics & Toiletries, vol. 106, December 1991, pp. 49–52, the disclosure of which is incorporated herein by reference. This technique is based on the following: an emulsion is prepared (introduction of water into oil) at a temperature which must be higher than the phase inversion temperature (or PIT) of the system, i.e., the temperature at which the equilibrium between the hydrophilic and the lipophilic properties of the emulsifier(s) used is reached; at elevated temperature (>PIT) the emulsion is of the water-in-oil type and, as it cools, at the phase inversion temperature, this emulsion is inverted to become, this time, an emulsion of the oil-in-water type, and does so by having first passed through a microemulsion state.

An emulsion according to the invention can be obtained by a phase inversion process, wherein the following are mixed:

(A) at least one cosmetic oil,
(B) at least one nonionic emulsifier having an HLB ranging from 9 to 18, and
(D) water, and optionally
(E) adjuvants which are stable at the phase inversion temperature, in order to obtain a conventional emulsion. The emulsion is then heated to a temperature at or above the phase inversion region or the emulsion is prepared at such a temperature that in a second step the emulsion is then cooled to a temperature lower than the phase inversion region. At least one foaming surfactant (C) is introduced into this emulsion to obtain a homogeneous mixture and optionally the emulsion obtained is diluted further with water. Adjuvants (E) maybe added.

The phase inversion temperature region is established for a given composition by measuring the conductivity of a sample of the composition which is heated. When the phase inversion region is reached the conductivity of the emulsion increases very rapidly. In the phase inversion region it is possible to observe an increase in the conductivity from approximately 50 microsiemens per centimeter over a temperature range of 5 to 15° C., whereas it will be only approximately 5 microsiemens per centimeter over an equivalent temperature range outside the phase inversion region.

The nature of the oil phase forming part of the composition of the emulsions according to the invention is not critical and it can thus comprise of any compounds that are already generally known as being suited for the manufacture of emulsions of the oil-in-water type. In particular, these compounds may be selected from the various fatty substances, oils of vegetable, animal or mineral origin, natural or synthetic waxes, and the like, and mixtures thereof.

Among the oils that can be employed in the present invention, mention may be made of oils of vegetable or animal origin, such as, for example, perhydrosqualene, squalane, copra oil, macadamia oil, castor oil, turtle oil, soya oil, grapeseed oil, sesame oil, corn oil, rape oil, sunflower oil, cotton oil, avocado oil, olive oil, castor oil, jojoba oil and groundnut oil; hydrocarbon oils, such as paraffin oils and liquid petrolatum; silicone oils, such as, polymethylsiloxanes, polymethylphenylsiloxanes, polysiloxanes modified with fatty acids, polysiloxanes modified with fatty alcohols, polysiloxanes modified with polyoxyalkylenes, fluorinated silicones, perfluoro and/or organofluoro oils; higher fatty acids, such as myristic acid, palmitic acid, stearic acid, behenic acid, oleic acid, linoleic acid, linolenic acid and isostearic acid; higher fatty alcohols, such as cetanol, stearyl alcohol and oleyl alcohol; and mono- and diesters corresponding to one of the following formulae (I) (II) or (III):

$$R^1\text{—COOR}^2 \qquad (I)$$

$$R^2\text{OOC—R}^3\text{—COOR}^2 \qquad (II)$$

$$R^1\text{—COOR}^3\text{OOC—R}^1, \qquad (III)$$

wherein $R^1$ and $R^2$ represent alkyl groups containing from 1 to 22 carbon atoms or alkene groups containing from 8 to 22 carbon atoms, $R^3$ represents an alkanediyl group containing from 2 to 16 carbon atoms, the esters containing at least 10 carbon atoms. Among these latter compounds, mention may be made of, in particular, isopropyl myristate, isopropyl palmitate, butyl stearate, hexyl laurate, isononyl isononanoate, 2-ethylhexyl palmitate, 2-hexyldecyl laurate, 2-octyidecyl palmitate, 2-octyldodecyl myristate, di-2-ethylhexyl succinate, diisostearyl malate, 2-octyldodecyl lactate, glyceryl triisostearate, glyceryl triisostearate, di-n-butyl adipate, di(2-ethylhexyl) adipate, ethylene glycol dioleate, ethylene glycol diisotridecanoate, ethylene glycol diisostearate and neopentyl glycol dicaprylate.

The oil phase, may, of course, also contain one or a number of conventional lipophilic cosmetic adjuvants.

The nonionic emulsifiers which can be employed in the present invention may be selected from compounds comprising a lipophilic residue selected from, for example, $C_6$–$C_{30}$ alkyl or acyl functional groups and, compounds comprising a hydrophilic residue selected from, for example, glycol and glucose groups and polyol ethers. Their HLB balance may range from 9 to 18, and preferably an emulsifier having an HLB ranging from 9.5 to 11.5 is selected. The HLB balance (hydrophilic-lipophilic balance) of an emulsifier is calculated according to the following formula:

$$HLB=(100-L)/5$$

in which L denotes the weight percentage of the lipophilic group (that is of the $C_6$–$C_{30}$ alkyl or acyl group) relative to the weight of the whole molecule.

As nonionic emulsifiers preferably employed in the present invention, mention may be made of, in particular, the addition products of ethylene oxide and fatty alcohols containing from 6 to 30 carbon atoms or partial esters of polyols containing from 3 to 16 carbon atoms and of fatty acids containing from 14 to 22 carbon atoms. The addition products of ethylene oxide to fatty alcohols are available commercially. The addition products of ethylene oxide to partial esters of polyols and of fatty acids can be easily obtained by ethoxylation of partial fatty acid esters of glycerol or of fatty acid mono- or diesters of sorbitol.

Preferably, the emulsifier employed corresponds to the formula (IV):

$$R^4\text{—(O—CH}_2\text{—CH}_2)_n\text{—OH} \qquad (IV)$$

wherein $R^4$ represents a branched or linear, saturated or unsaturated hydrocarbon residue containing from 8 to 28 carbon atoms and n represents a number ranging from 8 to 50, preferably from 8 to 30. It is also possible to employ an addition product of from 4 to 20 moles of ethylene oxide and one or a number of partial esters of glycerol. Partial esters of glycerol are intended to mean, for example, mixtures of $C_{10}$–$C_{20}$ fatty acid mono-, di- and triglycerides obtained by esterification of one mole of glycerol with 1 or 2 moles of a $C_{10}$–$C_{20}$ fatty acid. More preferably, the emulsifier employed is the product of condensation of behenyl alcohol and of 9 ethylene oxides.

The emulsions according to the invention include at least one foaming surfactant which is selected from anionic, cationic, nonionic and amphoteric foaming surfactants.

The foaming surfactants employed according to the present invention are selected from those having a foamability characterized by a foam height greater than 10 mm when measured according to the Ross-Miles method in the case of a solution containing 0.02% by weight of surfactant (active substance) in distilled water at 25° C.

The following foaming surfactants are preferably employed in the present invention.

In the category of foaming anionics:

alkyl phosphates, such as, for example, sodium lauryl phosphate;

alkyl taurates, such as, for example, sodium methyl palmitoyl taurate;

sulfosuccinates, such as, for example, cocoyl sulfosuccinate or the disodium salt of oxyethylenated lauryl alcohol sulfosuccinate;

alkyl sulphates, such as, for example, triethanolamine lauryl sulfate;

sarcosinates, such as, for example, sodium lauroyl sarcosinate;

alkyl ether sulfates, such as, for example, sodium lauryl ether sulphate;

isethionates, such as, for example, sodium cocoyl isethionate; and alkyl ether carboxylates, such as, for example, oxyethylenated sodium decyl ether carboxylate.

In the category of foaming nonionics:

polyglyceryl alkyl ethers such as, for example, polyglycerolated dodecanediol; and alkylglucosides such as, for example, decyl glucoside.

In the category of foaming cationics:

amine oxides; and quaternary ammonium salts like, for example, polyquaternium 22 (INCI nomenclature).

In the category of foaming amphoterics:
betaines such as, for example, disodium cocoamphodiacetate, cocamidopropylbetaine and cocobetaine.

In addition, the emulsions according to the invention may include at least one coemulsifier in a quantity such that the combination of the emulsifiers and coemulsifiers ranges from 0.5 to 30% of the total of the emulsion, and preferably from 2 to 10% of the emulsion. The coemulsifiers may represent up to 50% by weight of the combination of the emulsifiers and coemulsifiers. This coemulsifier is selected from $C_{12}$–$C_{22}$ fatty alcohols or the partial esters of $C_2$–$C_6$ polyols with $C_{12}$–$C_{22}$ fatty acids. Preferably $C_{12}$–$C_{22}$ glycerol fatty esters are employed.

The emulsions according to the invention comprise from 10 to 90% of water and preferably from 40 to 60%. Water usually is intended to mean pure water. However, a proportion of the water employed in the emulsions according to the invention may optionally be selected from mineral or thermal waters. In general a mineral water is suitable for consumption, which is not always the case with a thermal water. Each of these waters contains, inter alia, dissolved minerals and oligoelements. These waters are known for being employed for the purpose of specific treatment, depending on the oligoelements and the particular minerals which they contain, such as the hydration and desensitization of the skin or the treatment of some forms of dermatitis. Mineral or thermal waters will denote not only natural mineral or thermal waters, but also natural mineral or thermal waters enriched in mineral constituents and/or in additional oligoelements, as well as mineral and/or oligoelemental aqueous solutions prepared from purified (demineralized or distilled) water.

A natural thermal or mineral water employed according to the invention may, for example, be selected from VITTEL water, VICHY basin water, URIAGE water, ROCHE POSAY water, BOURBOULE water, ENGHIEN-LES-BAINS water, SAINT GERVAIS-LES-BAINS water, N ÉRIS-LES-BAINS water, ALLEVARLES-BAINS water, DIGNE water, MAIZIÈRES water, NEYRAC-LES-BAINS water, LONS-LE-SAUNIER water, LES EAUX BONNES water, ROCHEFORT water, SAINT CHRISTAU water, FUMADES water and TERCIS-LES-BAINS water.

The dispersant aqueous phase may contain water or a mixture of water and of polyhydric alcohol(s), such as, for example, glycerol, propylene glycol and sorbitol or else a mixture of water and of water-soluble lower alcohol(s) such as ethanol, isopropanol or butanol (hydroalcoholic solution), and it may, of course, additionally contain water-soluble conventional cosmetic adjuvants. This aqueous phase usually represents from 50 to 95% of the composition, and preferably from 70 to 90%.

The cosmetic or dermatological emulsions of the invention may, in addition, contain: (E) water-soluble or liposoluble adjuvants which are usual in the cosmetic field, such as preservatives, antioxidants, perfumes, screening agents, colorants and hydrophilic or lipophilic agents.

The agents for the skin may be antiaging agents, antiwrinkle agents, hydrating or moisturizing agents, slimming agents, depigmenting agents, agents against free radicals (radical oxygen species), nutrient agents, protective agents, restructuring agents, firming agents, antiacne agents, exfoliating agents, emollient agents or agents for treating skin diseases like mycosis, dermatitis, psoriasis and the like. Depending on their nature, these agents are employed in the usual proportions of microemulsions, and, for example, range from 0.01% to 10% by weight relative to the total weight of the microemulsion.

A fourth subject of the present invention is the use of the emulsions according to the invention, such as defined above, as, or for the manufacture of, cosmetic and/or dermatological compositions for application to the skin or to hair, in particular for the cleansing and the care of the skin.

The process of cosmetic treatment of the skin or of hair comprises applying to the skin or hair an effective amount of a cosmetic composition as defined above.

Examples are given below in order to illustrate the subject-matter of the invention.

EXAMPLES

The percentages given in the examples were calculated by weight.

The viscosity of the emulsions is given in mPa.s. It was measured at 25° C. with the aid of a Brookfield viscometer equipped with a module (module I) turning at a speed of 200 tr/min.

Example 1

| Phase 1 | |
| --- | --- |
| dicapryl ether | 7.7% |
| isocetyl stearate | 3% |
| cetearyl isononanoate | 4% |
| beheneth-9 | 4.5% |
| Phase 2 | |
| distilled water | 14.5% |
| preservative | q.s. |
| Phase 3 | |
| distilled water | q.s. 100 |
| sodium lauryl ether sulphate | 5% |

Procedure:

Phases 1 and 2 were heated separately to 60° C. and homogenized. Phase 2 was poured slowly, with stirring, onto phase 1 and the mixture was heated as far as the phase inversion temperature, which was around 85° C. The emulsion obtained became virtually transparent and bluish. The heating was stopped and phase 3 was poured in unheated and the mixture was allowed to cool while slow stirring was maintained. The viscosity of the emulsion was 3.5 mPa.s.

The composition obtained was introduced into an aerosol receptacle which was pressurized with isobutane in a weight proportion 97/3. The contents were translucent and perfectly stable after several months' storage. A pressure applied to the dispensing head of the receptacle made it possible to restore and dispense a creamy foam which was employed as a hydrating cleanser for the face.

Example 2

| Phase 1 | |
| --- | --- |
| ceteareth-12 | 3% |
| glyceryl stearate | 2% |
| octyl palmitate | 10% |
| dioctyl adipate | 10% |
| Phase 2 | |
| distilled water | 20% |
| glycerol | 3% |

-continued

| Phase 3 | |
|---|---|
| distilled water | q.s. 100 |
| preservative | q.s. |
| decyl polyglucose | 5% |
| cocoylamidopropylbetaine | 5% |

The same procedure as in Example 1 was followed to obtain a foaming emulsion for removing make-up, which was restored and dispensed in the form of a creamy foam which left the skin clean and soft after application and rinsing. The viscosity of the emulsion was 5.9 mPa.s.

Example 3

| Phase 1 | |
|---|---|
| dicapryl ether | 7% |
| isocetyl stearate | 7% |
| hexyl laurate | 1.5% |
| beheneth-9 | 4.5% |
| Phase 2 | |
| distilled water | 17.5% |
| sodium pyrrolidonecarboxylate | 3% |
| Phase 3 | |
| distilled water | q.s. 100 |
| preservative | q.s. |
| sodium lauryl ether sulphate | 5% |
| decylglucoside | 3% |

The same procedure as in Example 1 was followed to obtain a hydrating foaming emulsion which was restored and dispensed in the form of a creamy foam. The viscosity of the emulsion was 2.6 mPa.s.

What is claimed is:

1. An aerosol pressurized device comprising a pressurized receptacle, said receptacle containing a propellant gas and a foaming pressurizable oil-in-water emulsion comprising:
   (A) from 10 to 30% by weight of at least one cosmetic oil;
   (B) from 2 to 10% by weight of at least one non-ionic emulsifier having an HLB from 9 to 12, wherein said non-ionic emulsifier is:
      (i) an addition product of ethylene oxide and a fatty alcohol containing 6 to 30 carbons, or
      (ii) an addition product of ethylene oxide and a partial ester of a $C_3$–$C_{16}$ polyol and a $C_{14}$–$C_{22}$ fatty acid,
   (C) from 5 to 15% by weight of at least one anionic, cationic, non-ionic or amphoteric foaming surfactant, wherein said foaming surfactant is a polyglyceryl alkyl ether, an alkylglucoside, an alkylphosphate, an alkyl taurate, a sulphosuccinate, an alkyl sulfate, a sarcosinate, an alkyl ether sulphate, an isethionate, an alkyl ether carboxylate, an amine oxide, a quaternary ammonium salt, or a betaine,
   (D) from 40 to 60% by weight of water,
   wherein the oil phase of the oil-in-water emulsion comprises oil particles having a particle size ranging from 50 to 1000 nm, and the ratio of the weight of the oil to the weight of the foaming surfactant is greater than or equal to 1.

2. An aerosol pressurized device according to claim 1, wherein said oil-in-water emulsion has been prepared by a phase inversion method.

3. An aerosol pressurized device according to claim 1, wherein the particle size of said oil particles ranges from 70 to 350 nm.

4. An aerosol pressurized device according to claim 1, wherein the particle size of said oil particles ranges from 100 to 300 nm.

5. An aerosol pressurized device according to claim 1, wherein approximately 90% of said oil particles have a particle size ranging from 100 to 300 nm.

6. An aerosol pressurized device according to claim 1, wherein said at least one foaming surfactant is capable of producing a foam height greater than 10 nm when measured according to the Ross-Miles method in a solution containing 0.02% by weight of said foaming surfactant in distilled water at 25° C.

7. An aerosol pressurized device according to claim 1, wherein the combination of said at least one nonionic emulsifier and at least one co-emulsifier comprises from 0.5 to 30% by weight of the total emulsion.

8. An aerosol pressurized device according to claim 1, wherein the combination of said at least one nonionic emulsifier and at least one co-emulsifier comprises from 2 to 10% by weight of the total emulsion.

9. An aerosol pressurized device according to claim 1, wherein said oil-in-water emulsion comprises mineral water or thermal water.

10. An aerosol pressurized device according to claim 1, wherein said oil-in-water emulsion has a Brookfield viscosity measured at 25° of less than or equal to 20 mPa.s.

11. An aerosol pressurized device according to claim 1, wherein said oil-in-water emulsion has a Brookfield viscosity measured at 25° of less than or equal to 10 mPa.s.

12. An aerosol pressurized device according to claim 1, wherein said weight ratio is greater than or equal to 1.

13. An aerosol pressurized device according to claim 12, wherein said weight ratio is greater than or equal to 2.

14. An aerosol pressurized device according to claim 1, wherein said at least one nonionic emulsifier is a compound having a lipophilic residue which is a $C_6$–$C_{30}$ alkyl or acyl functional group, a compound having a hydrophilic residue which is a glycol or glucose group, or a polyol ether.

15. An aerosol pressurized device according to claim 1, wherein aid at least one nonionic emulsifier has an HLB ranging from 9.5 to 11.5.

16. An aerosol pressurized device according to claim 1, wherein said at least one nonionic emulsifier is:
   (a) a compound of formula (IV):

$$R^4-(O-CH_2-CH_2)_n-OH$$

wherein $R^4$ represents a branched or linear, saturated or unsaturated hydrocarbon residue containing from 8 to 28 carbon atoms and n represents a number ranging from 8 to 50, or
   (b) an addition product of 4 to 20 moles of ethylene oxide and at least one $C_{14}$–$C_{22}$ fatty acid partial ester of glycerol.

17. An aerosol pressurized device according to claim 1 further comprising at least one co-emulsifier selected from partial esters of $C_2$–$C_6$ polyols with $C_{12}$–$C_{22}$ fatty acids, wherein the weight ratio of said at least one co-emulsifier to said at least one nonionic emulsifier is less than or equal to 1.

18. An aerosol pressurized device according to claim 1, further comprising at least one agent, wherein said agent is a water-soluble preservative, a liposoluble preservative, an antioxidant, a perfume, a screening agent, a colorant, a hydrophilic agent, or a lipophilic agent.

19. An aerosol pressurized device according to claim 1, wherein said at least one cosmetic oil is an oil of vegetable origin, animal origin, a silicone oil, a higher fatty acid, a higher fatty alcohol, or a mono- or diester chosen from formulas (I), (II), and (III)

$$R^1\text{—COOR}^2 \quad (I)$$

$$R^2\text{OOC—}R^3\text{—COOR}^2 \quad (II)$$

$$R^1\text{—COOR}^3\text{OOC—}R^1, \quad (III)$$

wherein $R^1$ and $R^2$ denote alkyl groups containing from 1 to 22 carbon atoms or alkene groups containing from 8 to 22 carbon atoms, and $R^3$ denotes an alkanedioyl group containing from 2 to 16 carbon atoms, wherein the mono- and diesters contain a total of at least 10 carbon atoms.

20. An aerosol pressurized device according to claim 1, wherein said at least one nonionic emulsifier is an addition product of ethylene oxide and a fatty alcohol containing from 6 to 30 carbons.

21. An aerosol pressurized device according to claim 1, wherein the weight ratio of said at least one cosmetic oil to said at least one foaming surfactant is greater than or equal to 0.5.

* * * * *

UNITED STATES PATENT AND TRADEMARK OFFICE
CERTIFICATE OF CORRECTION

PATENT NO. : 6,620,855 B2
DATED : October 7, 2003
INVENTOR(S) : Raluca Lorant

It is certified that error appears in the above-identified patent and that said Letters Patent is hereby corrected as shown below:

<u>Column 10,</u>
Lines 29 and 32, "25º of" should read -- 25º C of --.
Line 43, "aid" should read -- said --.

Signed and Sealed this

Twenty-fifth Day of November, 2003

JAMES E. ROGAN
*Director of the United States Patent and Trademark Office*